United States Patent [19]

Moon et al.

[11] Patent Number: 4,804,950

[45] Date of Patent: Feb. 14, 1989

[54] TABLE DRIVEN MULTICHANNEL DATA ACQUISITION AND DISPLAY FOR SIGNAL MONITORING

[75] Inventors: James B. Moon, Portland; Don L. Clark, Hillsboro, both of Oreg.

[73] Assignee: SpaceLabs, Inc., Bothell, Wash.

[21] Appl. No.: 796,048

[22] Filed: Nov. 7, 1985

[51] Int. Cl.$^4$ .............................................. G09G 1/00
[52] U.S. Cl. ................................... 340/715; 340/712; 340/721; 128/710
[58] Field of Search ............... 340/706, 712, 715, 717, 340/721, 722, 286 M, 525, 870, 11, 365 P; 364/518, 521, 550, 415; 128/709, 710, 712, 670, 419 PT

[56] References Cited

U.S. PATENT DOCUMENTS

| | | |
|---|---|---|
| 3,811,040 | 5/1974 | Weinfurt et al. ..................... 340/722 |
| 3,860,754 | 1/1975 | Johnson et al. ................... 340/365 P |
| 4,216,462 | 8/1980 | McGrath et al. .................... 128/710 |
| 4,303,973 | 12/1981 | Williamson, Jr. et al. ......... 340/722 |
| 4,356,475 | 10/1982 | Neumann et al. .................... 340/715 |

*Primary Examiner*—Gerald L. Brigance
*Assistant Examiner*—Jeffery A. Brier
*Attorney, Agent, or Firm*—Seed and Berry

[57] ABSTRACT

A method and system for patient monitoring wherein data acquired by parameter measuring modules is downloaded to an information processing and display station. Table data structures resident within the modules are downloaded to the display station during initialization of the module on the link. The tables completely define the number, functionality and visual attributes of all control keys associated with each channel of the module. The tables include: text and parse tables which define the number, size, attributes and text for each key; a process table which contains a plurality of control programs which are executed by an interpreter portion of the display software in response to activations of a control key; and a channel control table which modifies the operating conditions of the channel in response to preselected control keys. A module header table is provided which defines display memory requirements of the tables for the module's channels, and an active-module table provided by the display station maintains a list of modules active on the link and the location of the module header tables once they are downloaded.

28 Claims, 3 Drawing Sheets

TABLE DRIVEN MULTICHANNEL DATA ACQUISITION AND DISPLAY FOR SIGNAL MONITORING

BACKGROUND OF THE INVENTION

This invention relates to a multichannel data acquisition and display system; more particularly, to a table driven system for physiological monitoring.

Important considerations for improving medical patient monitors are flexibility in the number of physiological parameters to be monitored, addition and removal of parameters without causing interruption of other monitoring functions, avoidance of user selection of "parameter addresses", flexibility with respect to the location of the data acquisition hardware, and cost. In addition, it is important that future capabilities be easily integrated into the framework of the monitor hardware and software. The inability to predict the processing requirements of yet undefined data acquisition, signal analysis, and data reduction algorithms imposes a need to be able to easily expand the processing capabilities of the system by providing a processing capability for each physiological measurement.

SUMMARY OF THE INVENTION

An improved patient monitoring system including at least one parameter measuring module for data acquisition and an information processing and display station for managing the display of the data via control keys is provided. The modules are coupled to the display station via a data link. In the preferred embodiment the data link is a serial bit data link and the display station comprises a touch screen with control keys.

Table means resident in the module are downloaded over the link to the display station. The table means completely defines the number, functionality and visual attributes of all control keys associated with each channel of the module in such a way that the display station software needs to know only the nature of the data structure.

The table means includes a channel text table, a channel parse table, a channel process table, a channel status table and a channel control table for each channel of the module. The channel text table contains all the textual material to be displayed for the control keys associated with each channel. Text is stored as messages with one or more characters and means are provided for concatenating messages.

The parse table defines the parameters such as number, size, location and attributes of all the keys for each channel. The channel process table contains a plurality of control programs which are executed by an interpreter portion of the display station software in response to operator activated control keys or packets received from the module. The parse table further comprises information which relates each control key to a control program in the control table and text messages in the text table.

The channel control table modifies particular channel operation parameters in response to activation of preselected control keys and the module. Finally, a waveform buffer is provided in the display station memory for storing waveform data from preselected channels for display in display windows. In the preferred embodiment, at least twelve seconds of data can be stored in the waveform buffer.

A module header table is also provided which contains information about the display station memory requirements for sorting the channel tables for the channels of the associated module. An active module table is present in the display station and contains the identity of each module coupled to the data link and also contains the location of the modular header tables in the display memory once they are downloaded. A module sysgen table downloaded for the module contains the serial number and software revision number of the module.

DETAILED DESCRIPTION OF THE DRAWINGS

Figure 1:
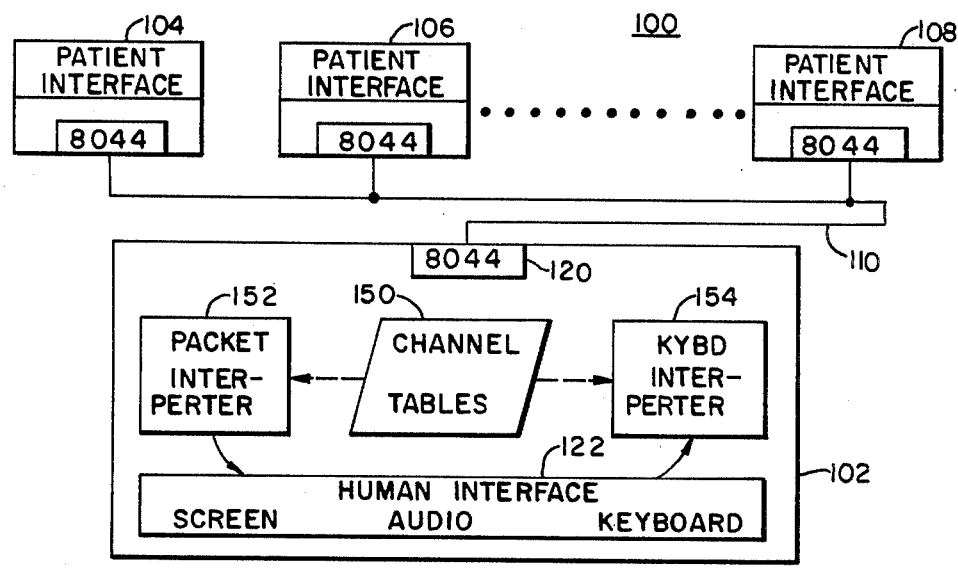
FIG. 1 is an overall block diagram of the preferred embodiment physiological monitoring system of the present invention.

Referring now to FIG. 1, a block diagram of a preferred embodiment physiological monitoring system designated generally 100 is shown. It comprises an information processing and display unit 102 and one or more parament measurement modules even numbers 104, 106 and 108. The unit 102 and modules 104 through 108 are coupled together in the preferred emboidment over a serial data link 110 although a serial data link is not necessary to practice the invention. In the preferred embodiment the unit comprises an Intel manufactured 8044 Remote Universal Peripheral Interface (RUPI) 120 and an Intel manufactured 80186 main processor not shown. The unit 120 controls communications on the network and controls display of the data on a display portion of the human interface 122.

Figure 2:
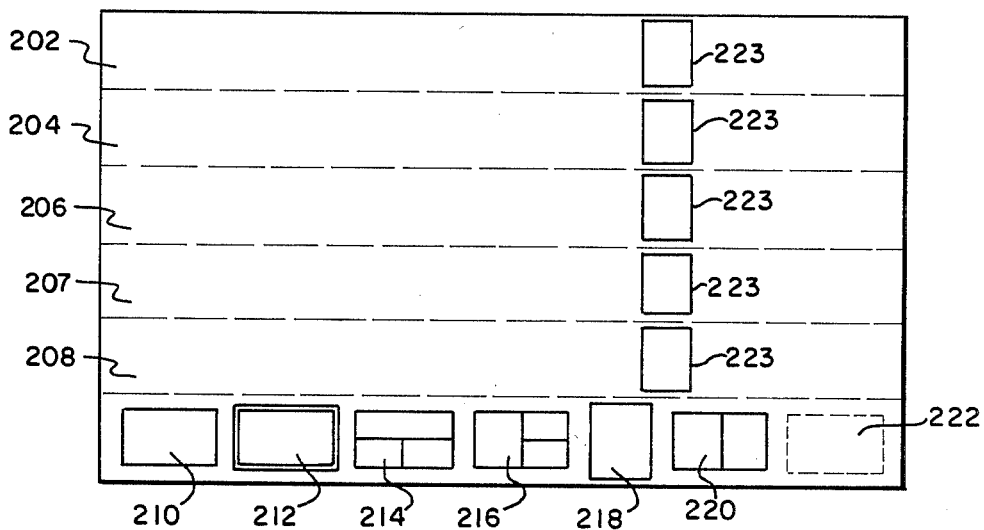
FIG. 2 is a block diagram representation of a display portion of FIG. 1.

In the preferred embodiment of the present invention the display portion of the human interface 122 is an infrared touch screen designated generally 200 and shown in more detail in FIG. 2. Infrared touch screens are well known in the art. See U.S. Pat. Nos. 3,764,813; 3,775,560; 3,860,754; 4,243,879; 4,267,443; and 4,384,201. Screen 200 is shown divided into a plurality of window regions 202, 204, 206, 207 and 208, each of which is assigned to display the data of one of the module channels. Located along the periphery of the display area, surrounding the window regions a plurality of touch zones or keys even numbers 210 through 222 are provided. The operator when touching one of these keys is enabled to control the system within the limits of the control function of the key. Contents of the display, setting of alarm limits in the module etc., can be controlled by the various touch keys.

Each of the modules 104, 106 and 108 comprises an 8044 RUPI and a patient interface. In general each module monitors a particular patient parameter or parameters. A module may comprise a single channel or a plurality of channels. For example, module 104 may be an ECG single channel module, while module 106 may include a single temperature channel and dual pressure channels. Module 108 can be some other variation of parameters to be measured. In the ECG module, for example, analog data is acquired by electrodes coupled to the patient. The data is digitized and processed by an ECG algorithm and prepared as a message for transmission over the data link 110 to the unit 102 where it will be displayed. The module, in addition, to its RUPI may require a dedicated processor for digitizing and processing the signal.

In the system of FIG. 1, the serial data link 110 follows the well known IBM Synchronous Data Link Control (SDLC) protocol (reference IBM publication GA27-3093-2, File No. GENL-09). It is a bit oriented, full duplex, serial by bit transmission, centralized control, synchronous, data communications message protocol. With this protocol, all of the communications are initiated by the unit 102, while a module receives only that data which is addressed to it, and transmits only when polled by the primary.

Figure 3:
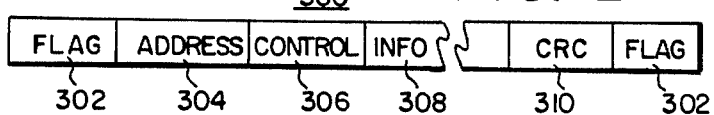
FIG. 3 is a block diagram of a frame of the Synchronous Data Link Control (SDLC) protocol used with the system of FIG. 1.

Referring now to FIG. 3, data is transmitted over the link 110 in frames 300 whose format is specified by SDLC. Briefly, a frame 300 includes a flag byte 302 at the beginning and end of each message, an address byte 304 which identifies the particular module in communication with the unit 102, a control byte 306, one or more message bytes in the information field 308 of the frame 300 and two bytes of error correction 310 before the end of message flag.

The SDLC protocol is transparent to the user since all bits added to the front and back of the message at the transmit end are removed at the received end. In the preferred embodiment the SDLC protocol is implemented by the unit 102's RUPI (primary RUPI) and the modules' RUPIs.

Figure 4:
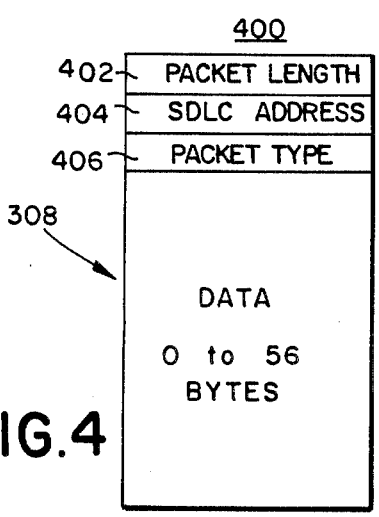
FIG. 4 is a block diagram of a packet of data as used by an information and display processing unit portion of FIG. 1.

Referring now to FIG. 4, the data to be transferred over the network 100 is formatted in such a way that the primary 8044 can determine the boundaries of the data blocks to be transmitted to a particular module, and in such a way that the primary 8044 can separate data received from the modules into meaningful blocks for processing by the unit 102. For this reason, the data is formatted in packets 400. The first two bytes of each packet are not part of the information field of each SDLC frame, but are appended to or stripped from the data by the primary 8044 depending on the direction of transfer. The length byte 402 determines the number of bytes in the packet. The "SDCL address" byte 404 indicates the module which was the source of the data, or to which the data is to be transferred. The remaining bytes of the packet are the information field 308 of the SDLC protocol, the first byte of which 406 is the "packet type" byte which defines the nature of the data.

Figure 8:
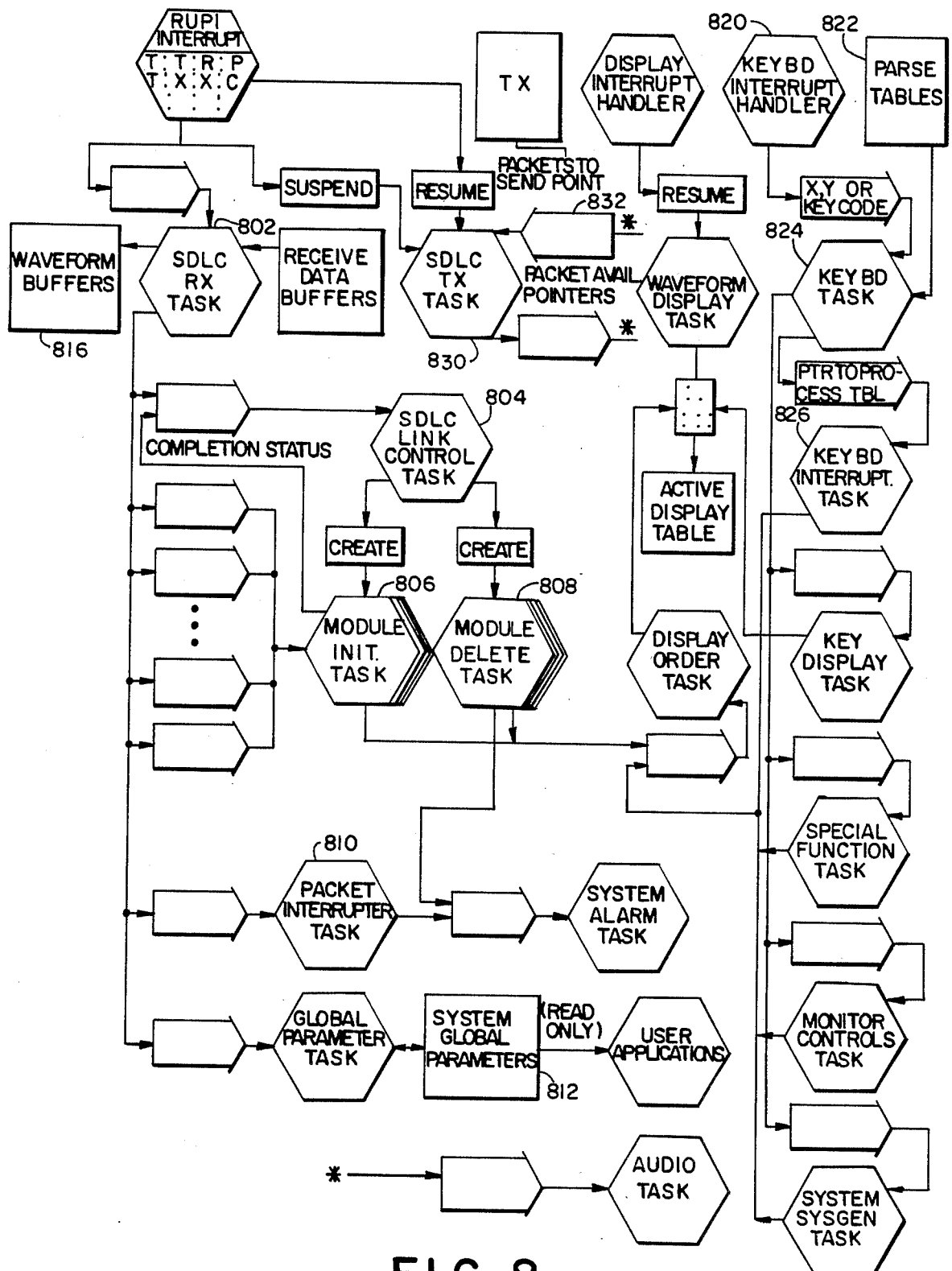
FIG. 8 is a block diagram of the tasks performed by the display software of the informtion and display processing station of FIG. 1.

In accordance with the present invention, each of the modules determines the human interface characteristics associated with its measurements for each channel by means of dedicated module and channel tables designated generally 150 which the module supplies to the information processing and display unit 102 during its initialization on the serial data link. By means of those tables 150 the module is able to control the manner in which information of each of its channels is displayed within the display windows 202, 204, 206, 207 and 208 on the unit 102's display device 200 as well as the characteristics of the keys 210 through 222 that are available to the operator. The information processing and display unit 102 includes display software which further comprises packet interpreter software 152 and keyboard interpreter software 154 which are capable of executing a specific set of instructions in order to carry out the commands specified in the tables 150. In the preferred embodiment, the keyboard interpreter 154 is an exact copy of the packet interpreter 152. A task diagram of the display software 800 is provided in FIG. 8.

The use of the tables 150, which are preprogrammed and reside in an associated module, such as one of the modules 104, 106 or 108, and which are downloaded to the unit 112 during initialization, eliminates costly revisions and modifications to extensive software programs which would be needed to operate a central information processing and display station using prior art unintelligent modules which serve merely as remote data acquisition and signal processing units and rely on the central station to organize every detail of the display of the data. Further, in the preferred embodiment, because of the tables 150, the type of microprocessor, the operating system details, and specific operation of the display hardware are of little or no consequence to the data acquisition and signal processing aspects of exisitng or future parameter measuring modules.

The display software 800 performs the functions of module address assignment and communications control as well as data packet routing. During the initialization of a module on the link 110 (tasks 802, 804 and 806), the software 800 transmits a series of commands to the module requesting its specific tables 150. As these tables are received the software stores them in the unit 102's memory and creates the software linkage necessary for the remainder of the system to be able to access them correctly. After the completion of the initialization phase, the display software routes the received packets from the modules to either the interpreter software 152 (tasks 802 and 810) or specified data buffers (e.g. 812) used by the interpreter 152 and display functions.

Figure 5:
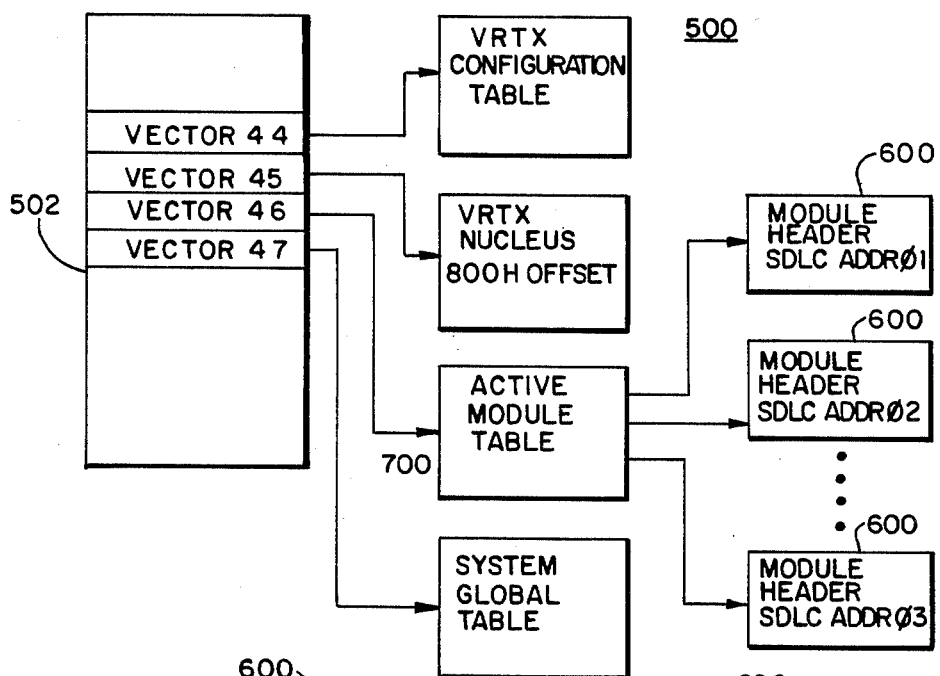
FIG. 5 is a block diagram mainly of station tables resident in the information and display processing station of FIG. 1.

Referring now to FIG. 5, the system tables designated generally 500 are a structure which enables all of the characteristics of the modules and their associated channels to be both described and located within the memory space of the information processing and display unit 102. The key aspects of the system tables relate primarily to those tables having to do with the downloadable configuration information which comes from the modules during their initialization phase.

As shown in FIG. 5, the interrupt vector table 502 points to various data structures within unit 102's memory including the data structure described as the Active Module Table 700. The Active Module Table 700 is essentially a data base representing all possible modules which can be plugged into the system with information about which ones are currently present and what their current state is, i.e. initialized or not initialized. Additional entries in the Active Module Table 700 point to other data structures described as the Module Header Tables 600 for which there is one associated with each possible module coupled to the system. The Module Header Table 600 in turn has information which describes the types of channels, numbers of channels, etc. which are part of that particular module.

Figure 6:
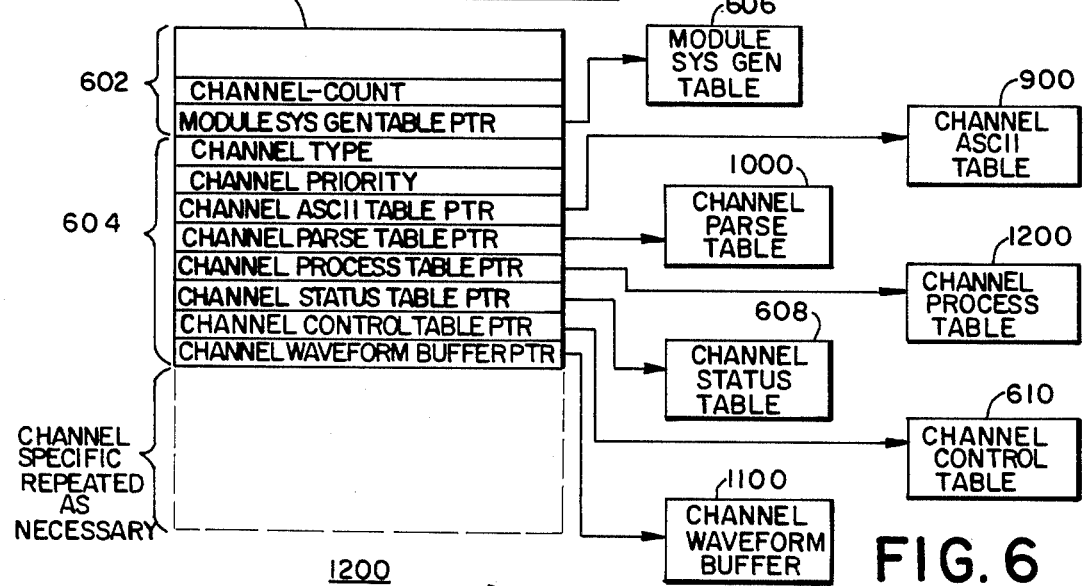
FIG. 6 is a more detailed block diagram of a Module Header Table resident in modules of FIG. 1.

The Module Header Table 600 in an abbreviated format and other associated tables are shown in FIG. 6.

The Module Header Table 600 comprises a module specific portion 602 and a channel specific portion 604 for each channel of the module. Portion 602 of the table contains a pointer to a table referred to as the Module SYSGEN table 606 which contains default conditions, that is control settings for the module and all of the channels in the module which are the assumed state at any time of initial power application. In addition, the Module SYSGEN table contains information regarding certain manufacturing information, i.e. module serial number, software revision levels, etc.

Portion 604 of the Module Header Table 600 has channel specific information. Each channel of the module is represented by a block of data within the table. The number of channels and corresponding blocks of data are indicated by the channel count found in the module specific portion 602 of the table. The channel specific portions of the Module Header Table 600 include: information such as the channel type, that is, ECG, pressure, temperature, etc.; the channel priority or where that channel should be displayed on the display screen relative to other channels in the system; and pointers to the remainder of the tables which describe that channel. These include pointers to the Channel ASCII Table 900, Channel Parse Table 1000, Channel Process Table 1200, Channel Status Table 608, Channel Control Table 610 and the Channel Waveform Buffer 1100. This channel specific portion 604 of the Module Header Table 600 is then repeated once for each channel in that particular module.

The Channel ASCII Table 900 is that table which contains text information pertaining to the operation of that channel. Table 900 is the basis for all prompting messages, labels of keys on the touch screen, help messages to explain the use of the various control keys and any other messages associated with alarms, fault detection, diagnostics, etc. The Channel ASCII Table 900 is static in nature, that is, once initialized and downloaded from the module, the Channel ASCII Table 900 is never modified during the course of normal operation. Provisions are made such that identical channels within the system can share a common ASCII Table such that memory space is not required for separate copies of this table when multiple channels of the same type and same version number are present in the system.

The Channel Parse Table 1000 in FIG. 6 is a table which defines all of the touch screen keys associated with that particular channel. Information contained in the Parse Tble 1000 includes: the size of the key and the location of the key on the screen; the characteristics of the key, i.e. single boxed, double boxed, split legends, vertically or horizontally lined; reverse video characteristics of all or portions of the key; blinking characteristics; dotted outlines, etc. The Channel Parse Table 1000 entries also include information to relate a particular key to a particular entry point in the Channel Process Table 1200 and contain pointers back to the Channel ASCII Table 900 to relate to particular message information.

The Channel Process Table 1200 is the table which contains the interpreter programs necessary to execute the desired functions when a key is pushed by the operator or when a data packet or alarm packet is received from the module via the serial data link. The Channel Process Table 1200 includes local variables which maintain the state information of certain functions. This table, as well as the Channel Parse Table 1000 are both variable in nature. That is, as the format of keys change or as the channel program proceeds through its execution, these tables are modified dynamically to reflect the current state of that channel.

The Channel Status Table 608 is a table which maintains the specific operating parameters of the channel at any point in time. Information included in the Channel Status Table comprises control settings, alarm limit settings, alarm enable/disable information and, basically, any other parameters which are available as controls to the operator. The Channel Status Table 608 is modified only by means of status packets sent down from the module and reflect what the module has indicated that its current status in fact is.

The Channel Control Table 610 is a table which is similar to the Channel Status Table 608 in that it is an image of the various control functions available for that channel. The Channel Control Table 610 however differs in that the intent is for the Channel Control Table 610 to reflect the desired control settings as indicated by the operator. For example, when an operator change occurs as a function of a key press, the Channel Process Table 1200 would typically modify the Channel Control Table 610 to indicate the new control settings which are desired and a copy of the Control Table 610 would be transmitted to the module. Upon receipt of the new control table image, the module would make any final decisions as to the legitimacy of that particular combination of control settings, take the appropriate actions to implement or deny those particular control settings, and echo a channel status packet which would then update the Channel Status Table 608 to reflect the actual control state of the module.

The Channel Waveform Buffer 1100 is a buffer which applies only to those channels which have waveform information, i.e., ECG or pressure, etc. Channels which have no waveform data, such as a temperature channel, do not have a Channel Waveform Buffer. They maintain a pointer to a Channel Waveform Buffer but the Channel Waveform Buffer length is zero. The Channel Waveform Buffer 1100 is that area where the physiological time related waveform information is stored typically. Waveform information typically includes twelve seconds worth of waveform history from which the data to be presented to the operator on the display or to be provided to a strip chart recorder is taken.

While not all of the tables in the system, these tables of FIG. 6 comprise the information downloaded from the module during its initialization phase and maintained during the course of the operation of the module. The tables include information about each channel of the module and they define all of the characteristics of the module and channels. They are independent of any prior information known to the display unit software prior to initializing that module.

The Active Module Table 700 is shown in more detail in Tables 1A-1C. The Active Module Table maintains the information relative to the number of modules present in the system and their current state. The first portion of the Active Module Table in Table 1A contains the basic information relative to each of the possible SDLC modules which can be accomplished on the network. In the preferred embodiment sixteen SDLC modules can be accommodated (bytes 3-18). For each module, a "present" bit indicates whether or not that address is currently assigned to a module resident on the SDLC data link 10.

TABLE 1
ACTIVE TABLE MODULE

| | 7 | 6 | 5 | 4 | 3 | 2 | 1 | 0 | |
|---|---|---|---|---|---|---|---|---|---|
| | LENGTH (14 HEX) | | | | | | | | 0 |
| | SDLC-ADDRESS (F0 HEX) | | | | | | | | 1 |
| | PACKET TYPE (10 HEX) | | | | | | | | 2 |

| | | 7 | 6 | 5 | 4 | 3 | 2-0 |
|---|---|---|---|---|---|---|---|
| SDLC CONTROLS FOR ADDRESS | 01H→ | PRESENT | 0 | ACTIVE | 0 | | RESERVED |
| | 02H→ | PRESENT | 0 | ACTIVE | 0 | | RESERVED |
| | 03H→ | PRESENT | 0 | ACTIVE | 0 | | RESERVED |
| | 04H→ | PRESENT | 0 | ACTIVE | 0 | | RESERVED |
| | 05H→ | PRESENT | 0 | ACTIVE | 0 | | RESERVED |
| | 06H→ | PRESENT | 0 | ACTIVE | 0 | | RESERVED |
| | 07H→ | PRESENT | 0 | ACTIVE | 0 | | RESERVED |
| | 08H→ | PRESENT | 0 | ACTIVE | 0 | | RESERVED |
| | 09H→ | PRESENT | 0 | ACTIVE | 0 | | RESERVED |
| | 0AH→ | PRESENT | 0 | ACTIVE | 0 | | RESERVED |
| | 0BH→ | PRESENT | 0 | ACTIVE | 0 | | RESERVED |
| | 0CH→ | PRESENT | 0 | ACTIVE | 0 | | RESERVED |
| | 0DH→ | PRESENT | 0 | ACTIVE | 0 | | RESERVED |
| | 0EH→ | PRESENT | 0 | ACTIVE | 0 | | RESERVED |
| | 0FH→ | PRESENT | 0 | ACTIVE | 0 | | RESERVED |
| | 10H→ | PRESENT | 0 | ACTIVE | 0 | | RESERVED |
| REMOTE BED CONTROLS | BED #1 | PRESENT | 0 | ACTIVE | 0 | | |
| | BED #2 | PRESENT | 0 | ACTIVE | 0 | | |
| | BED #3 | PRESENT | 0 | ACTIVE | 0 | | |
| | BED #4 | PRESENT | 0 | ACTIVE | 0 | | |

| | | | |
|---|---|---|---|
| MODULE HEADER POINTERS | MSB SDLC_ADDR_01H MODULE HEADER OFFSET LSB | 28/29 |
| | MSB SDLC_ADDR_01H MODULE HEADER SEGMENT LSB | 30/31 |
| | . . . | |
| | MSB SDLC_ADDR_10H MODULE HEADER OFFSET LSB | 88/89 |
| REMOTE BED HEADER POINTERS | MSB SDLC_ADDR_01H MODULE HEADER SEGMENT LSB | 90/91 |
| | MSB REMOTE BED #1 HEADER OFFSET LSB | 92/93 |
| | MSB REMOTE BED #1 HEADER SEGMENT LSB | 94/95 |
| | . . . | |
| SYSTEM FUNCTION HEADER POINTERS | MSB ALARM HEADER OFFSET LSB | 108/109 |
| | MSB ALARM HEADER SEGMENT LSB | 110/111 |
| | MSB MONITOR CONTROLS HEADER OFFSET LSB | 112/113 |
| | MSB MONITOR CONTROLS HEADER SEGMENT LSB | 114/115 |
| | MSB RECORD HEADER OFFSET LSB | 116/117 |
| | MSB RECORD HEADER SEGMENT LSB | 118/119 |
| | MSB SPECIAL FUNCTIONS HEADER OFFSET LSB | 120/121 |
| | MSB SPECIAL FUNCTIONS HEADER SEGMENT LSB | 122/123 |

The "active" bit indicates whether or not that module should be polled for information. The reserve field is intended for future use for implementation of dynamic polling algorithms based upon the actual data transfer requirements as indicated by the module.

In addition to Table 1A which contains information relative to the presence or absence and state of activity or inactivity of a module on the SDLC data link, Table 1B maintains pointer information to the Module Header Tables for the modules which are present on the data link. The module header pointers are determined by the display software 800 at the time that memory space is allocated for each of the Module Header Tables during the initialization of the modules. In all cases, the reference to pointers indicates a 16 bit offset and a 16 bit segment value consistant with the architecture of the Intel 8086 family of microprocessors.

The remaining elements of the Active Module Table in Table 1C contain information relative to Remote Bed Module Header Tables. System Function Header Tables and any other information which would be required to maintain the information about the system entities which the display unit must deal with.

As indicated in the previous section, the module header pointers are the link between the Active Module Table 700 and the Module Header Tables 600 which describe each of the module's present SDLC link.

The Module Header Table 600 is shown in more detail in Tables 2A-2D.

tical and repeated for each channel in this particular module.

Referring now to Table 2B, the first entry of the channel specific data block is the channel type, byte 12. The channel type indicates the nature of the measurement made by the particular channel, i.e., ECG, temperature, cardiac output, etc. Byte 13, the channel priority code, indicates the relative priority for display purposes of this channel versus other channels present in the system and is used by the display software to determine how to allocate the virtual windows (202, 204, 206, 207 and 208) of the display screen 200. The channel type

TABLE 2

| MODULE HEADER TABLE | | | | | | | | | |
|---|---|---|---|---|---|---|---|---|---|
| 7 | 6 | 5 | 4 | 3 | 2 | 1 | 0 | | BYTE |
| MSB | | | NEXT WRITE OFF | | | | LSB | | 0 |
| | | | | | | | | | 1 |
| MSB | | | MODULE HEADER LENGTH | | | | LSB | | 2 |
| | | | | | | | | | 3 |
| | | | RESERVED BYTE | | | | | | 4 |
| | | | CHANNEL COUNT | | | | | | 5 |
| MSB | | | MODULE SYSGEN TABLE OFFSET | | | | LSB | | 6 |
| | | | | | | | | | 7 |
| MSB | | | MODULE SYSGEN TABLE SEGMENT | | | | LSB | | 8 |
| | | | | | | | | | 9 |
| MSB | | | MODULE SYSGEN TABLE LENGTH | | | | LSB | | 10 |
| | | | | | | | | | 11 |
| | | | CHANNEL TYPE | | | | | | 12 |
| | | | CHANNEL PRIORITY | | | | | | 13 |
| | | | CHANNEL TYPE COUNT | | | | | | 14 |
| CH AVAIL | NO MEM | SPARE | SPARE | CH CONN | SPARE | C ALARMS | SPARE | | 15 |
| MSB | | | CHANNEL ASCII TABLE OFFSET | | | | LSB | | 16 |
| | | | | | | | | | 17 |
| MSB | | | CHANNEL ASCII TABLE SEGMENT | | | | LSB | | 18 |
| | | | | | | | | | 19 |
| MSB | | | CHANNEL ASCII TABLE LENGTH | | | | LSB | | 20 |
| | | | | | | | | | 21 |
| MSB | | | CHANNEL ASCII TABLE OFFSET | | | | LSB | | 22 |
| | | | | | | | | | 23 |
| MSB | | | CHANNEL ASCII TABLE SEGMENT | | | | LSB | | 24 |
| | | | | | | | | | 25 |
| MSB | | | CHANNEL ASCII TABLE LENGTH | | | | LSB | | 26 |
| | | | | | | | | | 27 |

The initial portion of the Module Header Table contains information specific to the module as a whole, e.g., information which is used during the initialization of Module Header table 600, namely, the length of the table at bytes 2 and 3 in Table 2A and the next right offset or the location of the next block of data when Module Header Table 600 is initialized from the module as a sequence of discontiguous packets of information.

The actual information used in the operation of the system begins with the fifth byte of data in Table 2A, the channel count information. This value indicates the number of independent channels which are implemented within this particular module and hence the number of data blocks which are repeated at the end of Module Header Table 600 for each channel. The Module SYSGEN table offset (bytes 6 and 7 in Table 2A) and table segment (bytes 8 and 9 in Table 2A) comprise the pointer to the Module SYSGEN Table 606 which will be described subsequently. The Module SYSGEN Table length (bytes 10 and 11 in Table 2A) is provided as part of Module Header Table 600 during its initialization process to indicate how much memory space will actually be needed for the Module SYSGEN Table when it is downloaded from the module.

The remaining sections of the Module Header Table, Tables 2B-2D, consist of blocks of data which are idencount, byte 14, is used to keep track of the number of channels in a system which may have the same exact functional purpose in monitoring a patient, i.e., two arterial pressure channels would be indicated and maintained such that the first initialized would have a channel type count of 0, the second one would have a channel type count of 1.

Byte 15 contains a number of flag bits which indicate that the channel is available, bit 7, i.e. it is ready for operation, and other aspects of the system. A no memory flag, bit 6, indicates that during the initialization attempt there was insufficient memory in the system to contain all of the tables associated with this particular channel. A channel connected flag, bit 3, indicates that the channel is in fact connected to the patient and should be initialized and made operable. When the input transducer to the channel is disconnected, bit 3 is cleared and the table space which would normally be associated with this channel can be made available for other system functions.

Finally there is an alarms flag, bit 1, indicating that the alarms associated with this channel have been disabled in their entirety and that there are no alarms enabled at all in this particular channel.

The remainder of the entries in the Module Header Table 600 in the channel specific portion contain the pointers comprising offset, segment and length values for the Channel ASCII Table 900, (bytes 16–21 in Table 2B), the offset and segment values for the Channel Parse Table 1000 (bytes 22–27 in Table 2B) and so on for the Channel Process Table 1200, the Channel Status Table 608, the Channel Control Table 610 and the Channel Waveform Buffer 1100 in Tables 2C and 2D. In addition to each of these pointer values, there is a length value. The length value having been provided during the initialization process to indicate to the display software how much memory must be allocated for each of the tables for the channel. The software then provides the offset and segment pointers.

The Module ASCII Table 900 is shown in Tables 3A-3B This Table as indicated previously contains all of the text information associated with the operation of a particular channel. Provision has been made for channels of like type and version number to be able to share the same Module ASCII Table. As with other tables, the initial information in the Table are those pieces of information needed during this initialization process of the table. The first items in Module ASCII Table 900 are the word version number which indicates the version of the ASCII table for validation that tables can be shared, and the use count indicating how many channels are currently sharing the same ASCII Table.

Following these items, the message count, bytes 6 and 7 in Table 3A, indicates the total number of independent text string messages which the table contains. The information following the message count is a message offset lookup table, i.e., a set of index values for the beginning locations of each numbered message in the table.

TABLE 2
MODULE HEADER TABLE (con't)

| MSB | Field | LSB | Byte |
|---|---|---|---|
| MSB | CHANNEL PROCESS TABLE OFFSET | LSB | 28, 29 |
| MSB | CHANNEL PROCESS TABLE SEGMENT | LSB | 30, 31 |
| MSB | CHANNEL PROCESS TABLE LENGTH | LSB | 32, 33 |
| MSB | CHANNEL STATUS TABLE OFFSET | LSB | 34, 35 |
| MSB | CHANNEL STATUS TABLE SEGMENT | LSB | 36, 37 |
| MSB | CHANNEL STATUS TABLE LENGTH | LSB | 38, 39 |
| MSB | CHANNEL CONTROL TABLE OFFSET | LSB | 40, 41 |
| MSB | CHANNEL CONTROL TABLE SEGMENT | LSB | 42, 43 |
| MSB | CHANNEL CONTROL TABLE LENGTH | LSB | 44, 45 |
| MSB | CHANNEL WAVEFORM TABLE OFFSET | LSB | 46, 47 |
| MSB | CHANNEL WAVEFORM TABLE SEGMENT | LSB | 48, 49 |
| MSB | CHANNEL WAVEFORM TABLE LENGTH | LSB | 50, 51 |

TABLE 3
MODULE ASCII TABLE

| MSB | Field | LSB | Byte |
|---|---|---|---|
| MSB | NEXT WRITE OFFSET ( WORD ) | LSB | 0, 1 |
| | LENGTH ( XX HEX ) | | 2 |
| | SDLC ADDRESS ( 01 TO 10 HEX ) | | 3 |
| | PACKET TYPE ( 56 HEX ) | | 4 |
| | RESERVED | | 5 |
| MSB | MESSAGE COUNT ( WORD ) | LSB | 6, 7 |
| MSB | MESSAGE OFFSET 0 ( WORD ) | LSB | 8, 9 |
| MSB | MESSAGE OFFSET 1 ( WORD ) | LSB | 10, 11 |
| MSB | MESSAGE OFFSET n ( WORD ) | LSB | 2n+4, 2n+5 |
| MSB | MESSAGE OFFSET n+1 ( WORD ) | LSB | |

MESSAGE OFFSET LOOKUP TABLE

Message zero has a starting point as indicated by message offset zero value (bytes 8 and 9) which indicates how far down into the table one must traverse in order to find the beginning of message zero. By implementing this index at the beginning of the Module ASCII Table 900, it is possible to incorporate any number of messages of any arbitrary length and maintain external software which does not have to change if the lengths of the individual messages should have to be changed. The final message offset indicated as message offset n+1 at bytes 2n+6 and 2n+7 in Table 3B is necessary because the lengths of the messages are determined by subtracting the offset of the message in question from the message offset of the next message. Hence, message offset n which points to the beginning of message n must be subtracted from message offset n+1 in order to determine the length of message n. While there is no message n+1 this message offset n+1 points to the first location in memory following the end of the table.

Referring to Table 3B, each message may be stored in one of two formats. It may be stored as a message text string itself, i.e., as a string of ASCII characters as indicated in Table 3B under the heading of Message Text (ASCII String). This string of characters comprises the total information necessary to determine the message. Special control characters within the ASCII text format are defined which indicate where certain pieces of variable information are to be inserted into the text string.

The second format in which a message may be stored may be in the form of a series of concatenated messages.

quired for each of the various modules and their respective channels.

Provisions for the insertion of substrings primarily in the form of variables are permitted within text strings. The insertion of a substring and the source (first byte) of that substring is indicated by a 1C, 1D or 1E hex character within the string. These character codes are normally ASCII control codes and serve no useful purpose in the display of text, and hence are used to indicate a particular substring insertion. These values indicate the insertion of a local channel dictionary variable, a global variable or a system ASCII Table string variable within the text. The bytes following this substring insertion indicator, indicate the manner in which the substring is to be inserted. If it is a variable, it can be indicated whether it is to be justified left or right within the length of the field, whether it is to be truncated, whether it is to be displayed as a floating point type of value and if it is, how many fractional bits are to be displayed if it is a numeric value. The second byte following indicates the total length of the field of text in which the particular variable is to be displayed and the third and fourth bytes indicate the offset or index value into the process table variable dictionary section where the number is to be found.

TABLE 3

MODULE ASCII TABLE (con't)

| | | |
|---|---|---|
| MESSAGE TEXT (ASCII STRING) | MESSAGE 0 CHARACTER 0 ( ASCII BYTE ) | 2n+6 |
| | MESSAGE 0 CHARACTER 1 ( ASCII BYTE ) | 2n+7 |
| | MESSAGE 0 CHARACTER n ( ASCII BYTE ) | |
| MESSAGE STRINGS TO CONCATONATE (LIST OF MESSAGE OFFSETS) | FF ( HEX ) | |
| | NUMBER TO CONCATONATE ( BYTE ) | |
| | MSB* MESSAGE OFFSET A ( WORD ) LSB | |
| | MSB* MESSAGE OFFSET B ( WORD ) LSB | |
| | MSB* MESSAGE OFFSET Z ( WORD ) LSB | |

The value FF in the first byte location of any particular message string indicates that that message string does not contain text itself, but rather a sequence of offset values to other messages which are to be concatenated or placed together end to end in order to form a final message. The first byte following the FF concatenation indicator is a binary number indicating from 1 up to 255, how many messages are to be concatenated to form the actual final message. Hence, there are provisions to allow the creation of libraries of words and phrases which can be formed together to form the actual message in question.

One of the bits in the message offset, the most significant bit, is used to indicate that the particular submessage of the total message is to be found in a system ASCII table which is not downloaded from the modules during initialization. Thus, a system ASCII table containing a library of words and phrases can be built and maintained which will reduce the table sizes re- Bytes 5 and 6 indicate in the case of an array type dictionary variable where that variable is to be found indexed relative to the beginning of the array.

Finally within the text fields it is possible to insert an attribute control code. This control code is indicated by a text character of value 1F hex. Whenever this value is encountered in the text string the next byte is to be interpreted as an attribute control byte. Some of the non-text attributes include the blink characteristic, reverse video characteristic, an underline characteristic, an intensify characteristic and selection of font size in the form of small, medium and large style character font as well as position information. The position information defines whether or not the text is to remain at the same base line, that is, vertical position, as previous text or whether it is to appear as a subscript, a superscript or to maintain the same center line in the case of a font size change.

Thus the ASCII Table provides for flexible display of text which can include direct text as indicated within the table, references to other text strings within the channel ASCII Table or within the system ASCII Table and the ability to insert variables, i.e. numeric values in the middle of a text string including the format in which they are to be displayed, as well as attribute control for the selection of font size and various attributes such as blank reverse video, underline, intensify, subscript and superscript.

Figure 7:
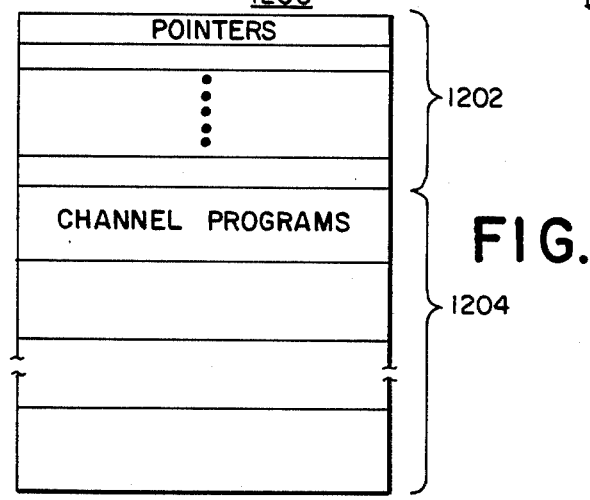
FIG. 7 is a more detailed block diagram of the Channel Process Table of FIG. 6.

The Channel Parse Table 1000 is given in Tables 4A–4D. Within the structure of the Channel Parse Table 1000 are several levels. The first portion in Table 4A is the overall information pertaining to the operator control key structures associated with the particular channel. The level count value, byte 4, indicates the number of levels within the tree structure of the Parse Table 1000, the level count being the maximum level of the longest branch of the tree. The version number is used for software maintenance purposes and in maintaining consistency from module to module. The exit index, bytes 6 an d7, is a value used to indicate which subprogram within the Channel Process Table 1200 of FIG. 7 should be used when the normal display or exit key of the touch screen 200 is invoked by the operator. Likewise the alarm menu offset, bytes 8 and 9, is a value used to indicate relative to the top of the Parse Table the level at which the alarm limits menu is located so that it can be invoked without having to transverse the entire tree structure.

The remainder of the description of the Parse Table 1000 comprises a number of similar data structures. The level zero data structure, Table 4B, relates to that level of the parse structure which represents those control keys visable to the operator when the particular channel is not being manipulated by the user, that is, the basic keys required to gain access to the remainder of the functions for that particular channel. It is unique in that it must include keys (223 in FIG. 2) which appear within the virtual waveform window assigned to that particular channel on the screen. Once one of these keys is invoked, all subsequent actions refer to keys which are displayed on the lower portion of the screen which is dedicated to the particular channel which the operator is manipulating at any particular point in time. The level key count, byte 10 in Table 4B, indicates how many keys are present within this particular level of the parse structure. Likewise the waveform key count, byte 11, indicates how many keys are to appear within the waveform zone assigned to that channel.

The alarm door open key count, byte 12, in the level zero data structure indicates how many keys are to be displayed during an alarm condition.

The open door key offset, bytes 15 and 16, indicates the position within the parse table where the primary control key for that module is defined. Likewise the alarm open door offset, bytes 17 and 18, indicates that level which is to be used to gain access to the controls of that channel when an alarm condition exists.

TABLE 4

CHANNEL PARSE TABLE

| 7 | 6 | 5 | 4 | 3 | 2 | 1 | BYTE |
|---|---|---|---|---|---|---|---|
| | XX HEX | | | | | | 0 * |
| | 01 TO 10 HEX | | | | | | 1 * |
| | 54 HEX | | | | | | 2 * |
| | CHANNEL NO ( BYTE ) | | | | | | 3 * |
| | LEVEL COUNT ( BYTE ) | | | | | | 4 * |
| | 01 DECIMAL | | | | | | 5 * |
| MSB | EXIT INDEX ( WORD ) | | | | | LSB | 6 / 7 |
| MSB | ALARM MENU OFFSET ( WORD ) | | | | | LSB | 8 / 9 |

TABLE 4

CHANNEL PARSE TABLE

| | |
|---|---|
| LEVEL KEY COUNT ( BYTE ) | 10 |
| WAVEFORM KEY COUNT ( BYTE ) | 11 |
| ALARM OPEN DOOR KEY COUNT ( BYTE ) | 12 |
| MSB   LEV 0 RESERVED ( WORD )   LSB | 13 / 14 |
| MSB   ( NUMERIC ) OPEN DOOR OFFSET ( WORD )   LSB | 15 / 16 |
| MSB   ALARM OPEN DOOR OFFSET ( WORD )   LSB | 17 / 18 |
| MSB   LEVEL EXIT INDEX ( WORD )   LSB | 19 / 20 |
| MSB   NEXT LEVEL LINE ( WORD )   LSB | 21 / 22 |

TABLE 4-continued

CHANNEL PARSE TABLE

| LOOKUP TABLE | | |
|---|---|---|
| | X 1 WAVEFORM WINDOW RELATIVE ( BYTE ) | XX |
| | Y 1 WAVEFORM WINDOW RELATIVE ( BYTE ) | +1 |
| | X 2 WAVEFORM WINDOW RELATIVE ( BYTE ) | +2 |
| | Y 2 WAVEFORM WINDOW RELATIVE ( BYTE ) | +3 |

In the levels other than level zero, e.g. Table 4C, the information is slightly different. There is a level key with the associated channel. In addition the Table 1000 contains a data block for each key.

TABLE 4

CHANNEL PARSE TABLE

| | | |
|---|---|---|
| | LEVEL KEY COUNT ( BYTE ) | YY |
| | SUB LEVEL COUNT ( BYTE ) | +1 |
| | ROW COUNT ( BYTE ) | +2 |
| | ROW HEIGHT ( BYTE ) | +3 |
| | START X ( BYTE ) | +4 |
| | START Y ( BYTE ) | +5 |
| | KEY SPACING ( BYTE ) | +6 |
| REPAINT | PROMPT INDEX ( WORD )  LSB | +7 +8 |
| MSB | LEVEL EXIT INDEX ( WORD )  LSB | +9 +10 |
| MSB | NEXT LEVEL LINK ( WORD )  LSB | +11 +12 | count byte YY as in level 0 and a sublevel count, byte +1. The sublevel count indicates how many sublevels, or how many additional sets of keys must be displayed in order to be able to display all the keys associated with a particular level within the parse structure. (In the preferred embodiment, 7 to 9 keys are the maximum that can be displayed at any one time.)

The row count, byte +2, and row height, byte +3, indicates the number of keys in a particular row and the height at which the keys are to be displayed. The start X and start Y values, bytes +4 and +5, respectively, indicate where on the screen the row of keys is to be displayed. The key spacing, byte +6, indicates the relative space between the keys.

The prompt index, bytes +7 and +8, is an index value into the Channel ASCII Table 900 where the prompt message associated with this particular level of the Parse Table is located. The level exit index, bytes +9 and +10, indicates the function to be performed by the Channel Process Table 1200 or by the interpreter 154 when the operator exits from a particular level of the parse structure back to the previous level by hitting the previous screen key on the monitor. Finally, the next level link, bytes +11 and +12, indicates the offset into the parse table at which the beginning of the data block for the next level down in the parse table exists. As described above the Channel Parse Table 1000 contains data defining the various key levels associated with the associated channel. In addition the Table 1000 contains a data block for each key.

A representative key data block is shown in Table 4D. Each key has a label and a help message indicated by the indexes, bytes 20 and 21 and bytes 22 and 23, respectively, at the beginning of their data structure. These are both indexes into the Channel ASCII Table 900.

The next three bytes, 24, 25 and 26, contain status bytes, status bits and reserve bits. Reserve bits are intended for future use. Three of the bits in the first byte contain access information, i.e., whether the particular key is valid at a central station, at a bedside unit or a remote bedside unit. The present bit indicates whether or not that key is to be momentarily removed from the list of keys or whether or not it should be displayed.

The redisplay bit in byte 25 is a flag indicating that something has been changed within the key (e.g., text information) which should be rewritten in order to update the key on the display.

The ASLRB bit (All Sublevels Replicate Bit) indicates that a particular key must appear within all sublevels of any particular multiscreen level of keys. This would apply, for example, to up arrow, down arrow keys in multiscreen alarm limits menus.

The repeat bit of byte 25 indicates that a particular key is to auto repeat if the user holds their finger on the key for an extended period of time. Inactive indicates that while the key exists and is displayed it is not currently to be acted upon.

The dotted bit in byte 25 indicates a dotted outline 222 in FIG. 2 for the key. The invisible bit means that it is present but it should not be displayed.

TABLE 4

CHANNEL PARSE TABLE

ACCESS STATUS ATTRIBUTE / DATA BLOCK REPEATED FOR EACH KEY:

| MSB | | | | | | | LSB | Byte |
|---|---|---|---|---|---|---|---|---|
| | | LABEL INDEX (WORD) | | | | | | 20, 21 |
| | | HELP INDEX (WORD) | | | | | | 22, 23 |
| RESERVED | RESERVED | RESERVED | RESERVED | RIGHTREV | RESERVED | RESERVED | PRESENT | 24 |
| REDISPLAY | ASLRB | RESERVED | RESERVED | REPEAT | INACTIVE | DOTTED | INVIS | 25 |
| SHAPE | SHAPED | FLASH | LEFTREV | RIGHTREV | REVERSE | RESERVED | DOUBLE | 26 |
| | | PAIRED KEY INDEX (BYTE) | | | | | | 27 |
| | | SUB LEVEL (BYTE) | | | | | | 28 |
| | | X WINDOW LOCATION (WORD) | | | | | | 29, 30 |
| | | Y WINDOW LOCATION (WORD) | | | | | | 31, 32 |
| | | KEY WIDTH (BYTE) | | | | | | 33 |
| | | KEY HEIGHT (BYTE) | | | | | | 34 |
| | | TASK INDEX (WORD) | | | | | | 35, 36 |
| | | NEXT LEVEL OFFSET (WORD) | | | | | | 37, 38 |

The shape zero and shape one bits of byte 26 indicate the basic nature of the key. Some of the options for the shape of the key are a whole key (210); a half key (214); a split key (216); or a vertical key (218). The left reverse, right reverse and reverse fields of byte 26 indicate that the left or right areas or split areas are to be individually displayed in reverse video or that the entire key is to be displayed in reverse video. Finally, the double bit indicates that the outline of the key is to be displayed as a double solid line 212 as opposed to a single solid line.

The paired key index, byte 27, indicates that certain keys must appear as pairs 220 in all cases and the index indicates the index into the other key which is its partner. The sublevel, byte 28, indicates at which sublevel of a parse table level a particular key is to be displayed while the X window location, bytes 29 and 30, and the Y window location, bytes 31 and 32, indicate relative to a window where a key is to be displayed if it is to be displayed in relative mode as opposed to absolute mode. The key width, byte 33, and key height, byte 34, define the size of the key. The task index, bytes 35 and 36, indicates the function or the task number within the Channel Process Table 1100 where the particular task is located associated with this key. A null value or zero value in this location indicates that no action is to take place when the key is pushed but only that a parse level change will occur.

Finally, the next level offset, bytes 37 and 38, indicates the beginning of the parse level which defines the keys to be displayed if this particular key is pushed. If the same level is to be maintained, the next level offset points to the same level within the parse table where the current parse structure is defined.

In summary, the purpose of the Channel Table data structures is to indicate the manner in which a module, during its initialization phase, can download channel information to the display unit which completely defines the number, the functionality and the visual nature of all the control keys to be associated with that particular channel in a way such that the display unit 102 software needs to know only the nature of the data structure but not the particular functions associated with any given channel.

The Channel Waveform Buffer is shown in detail in Table 5. The Channel Waveform Buffer is very simple in nature and is typically not initialized from the module. The only thing provided by the module is the length requirement of the Channel Waveform Buffer indicated in the Module Header Table 600. Once the waveform buffer space has been allocated as indicated by the length of the value in bytes 0 and 1, the remainder of the information in the buffer is either maintained by display software or consists of the actual waveform sample information which describes the waveform data itself. The oldest data index, bytes 2 and 3, indicates relative to the beginning of the buffer the location of the oldest in time information or waveform point contained in the buffer. This value will typically remain static until the entire buffer has been filled at which point the oldest data index will then begin to move as data is written over by new incoming data.

TABLE 5

| MSB | | LSB | Byte |
|---|---|---|---|
| | BUFFER LENGTH (WORD) | | 0, 1 |
| | OLDEST DATA INDEX (WORD) | | 2, 3 |
| | LAST TIME TAG (DOUBLE WORD) | | 4, 5, 6, 7 |

TABLE 5-continued

| — DELAY BUFFER (0) | WAVEFORM SAMPLE (oldest) (12 bits) | | | | LSB | 8 |
|---|---|---|---|---|---|---|
| DELAY BUFFER (1) | PACER | SYMBOL | INTENS | BLANK | MSB | 9 |
| | Note: Total number of waveform samples must be a multiple of 56 samples (112 bytes) | | | | | |
| DELAY BUFFER (n−1) | WAVEFORM SAMPLE (newest) (12 bits) | | | | | |
| — DELAY BUFFER (n) | PACER | SYMBOL | INTENS | BLANK | MSB | |

The last time tag, bytes 4 through 7, indicate the time of day in increments of one thirty second of a second since midnight of the time of day of the newest waveform information which has been loaded into the buffer.

Finally, the waveform information itself comprises two bytes or one word of information for each waveform data point. Each waveform sample consists of twelve bits of analog information and four flag bits which indicate whether a particular waveform point as represented by that sample data is to be intensified on the screen, blanked on the screen, whether or not a particular symbol is to be flashed on the screen, such as a heart symbol to represent the point at which a heartbeat was detected, and finally a bit called a pacer bit which is to flag those points on a waveform which may have been perturbed by a presence of a cardiac pacemaker.

The above description defines all of those tables which are common across all channel types. The remainder of the tables, such as the Channel Process Table, the Channel Control Table, the Channel Status Table, are dependent on the nature of the specific channel. The Channel Process Table 1200 in FIG. 7 includes programs written in an interpreted language specifically designed to facilitate the movement of data, the display of information, control of the parse table, and control of the status and control table. The instructions associated with those programs are totally independent of the type of post processor on which the interpreter 152 and 154 executes, that is, the Channel Process Table programs contain nothing in any way, shape or form which ties those programs to an 8086 family of microprocessor as has been used in this particular implementation. Rather, these interpretive programs such like any other form of high level computer language can be ported from one processor to another by rewriting the kernal or the interpreter execution software 152 and 154 which is resident in the display system unit 102 to host those programs on a different microprocessor.

In general the Channel Process Table 1200 comprises an index portion 1202 and a series of programs in portion 1204. During operation of a module, after initialization, packets received from the modules contain packet type numbers which identify an index location in portion 1202 of the Table 1200. The index number identifies the start of a program within portion 1204 that the packet interpreter 152 is to execute in order to handle the packet. The packet interpreter task 810 uses the SDLC and Channel number information in the packet to traverse the System Tables to find the Channel Process Table for the SDLC/Channel combination. Then, depending upon the type of packet, the interpreter 152 is invoked with pointers to the table and the data area, the program number to run and the SDLC/Channel values. Waveform packets bypass this step, however, and are routed directly to the Waveform Buffer 1100 by the software 802 and 816. Examples of packet types which require handling by the interpreter 152 are Channel Numeric Data (Packet Type 90H); Channel Limit Data (Packet Type 92H); Channel Status Data (Packet Type 94H); Channel Alarm Status (Packet Type 96H); and Channel Unformatted Message (Packet Type 98H).

The keyboard interpreter 154 handles commands entered by the operator through the keys on the touch screen. When a key is pressed the command carries with it a Process Table index found in the Parse Table (see 820, 822, 824 and 826 in FIG. 8).

When a module first becomes present on the datalink, an address is assigned to that particular module by dynamic address assignment algorithm and the display system software is made aware that a new module is present on the SDLC datalink. With that information the software 800 requests the Module Header Table 600 from the module. In response to this request, the module loads the display system memory with the Module Header Table 600 in a form of a sequence of packets of up to 56 bytes each until all of the module header data structure has been transferred. In its initial form, the Module Header Table 600 contains the length information required for each of the other tables but does not include any offset values where those tables are to be located in memory. The software 800 with the length information supplied in the Module Header Table 600 makes requests of a system utility known as the system memory manager for the allocation of memory space sufficient to hold the tables for that channel.

The memory space for each individual table is allocated separately so that the smallest usable blocks of memory in the system may be used for the channels of that particular module. When the memory space is allocated, software 800 in the display unit sends a request packet to the module (830, 832) indicating that a particular table should be loaded. In response to which the module again, as a series of packets of up to 56 bytes each, downloads the table in the form which represent accurately that particular channel's operation and status at its point of initialization. After all of the tables have been independently requested and downloaded from the module and stored in the main memory of the display unit. The software 800 informs various tasks in the display unit, such as, the display manager subsystem, the alarm subsystem, the user interface or touch screen key subsystem, that a new module and new channel is present in the system. At that point, the software 800 informs the channel through a command sent up the SDLC link (830) that it should begin its measurement function, that is, start sampling data from the patient, doing its necessary calculations and alarm limits checking, sending waveform information and numeric information and alarm information in the form of wavelength numeric and status packets and thusly causing information to be displayed on the screen. All of the functions associated with that display are taken from parameters in the tables. The entire format of the display windows, the size, functionality, visual attributes, labelling, etc. of control keys are determined by the tables as well as the actions to be taken and associated with an operator indicated command. Once operation has been established this process is continued until such time as a channel is to be deleted.

A channel may be deleted either because the input transducer to that channel was disconnected or because the operator physically unplugged or disconnected a particular module from the system. When one of these conditions exists, the detection of which goes beyond the nature of this description, the channel delete software which is the counterpart of initialization causes the channel to be made inoperable by setting its active bit in the Active Module Table zero and causing all of the memory space occupied by the tables of the channel in question to be returned to the system memory pool by returning the pointers to those tables to the system memory manager. When all the tables have been returned to the memory manager and all of the software subsystems, i.e. alarms subsystem, display manager subsystem, keyboard subsystem, etc. have been informed that the channel has been deleted. Then the channel is removed from the active module table and in total is gone from the system. It can be reinitialized at any time that it should reappear as being present on the SDLC link.

What is claimed is:

1. A signal monitoring system including at least one parameter measuring module having a plurality of channels for acquiring respective items of physiological data, and an information processing and display station having a plurality of control keys and a display device for managing the display of said physiological data on said display device, said system comprising:
    a data link coupling said at least one parameter measuring module to said information processing and display station; and
    table memory means resident with said at least one module containing a table to be downloaded over said data link to said station for controlling the operation of said station and for defining the number, functionality and visual attribututes of said control keys and data associated with each channel of the module to be displayed in said display device, whereby said information processing and display station is capable of displaying the data of each channel independently of the functions associated with the other channels once said table is downloaded to said station.

2. The system of claim 1 wherein said information processing and display station comprises a touch screen display and said control keys are activated through said touch screen.

3. The system of claim 1 wherein said data link comprises a serial bit data link.

4. The system of claim 1 wherein said table comprises a module header table for defining the memory requirements of the table associated with each channel of said module, and for storing the locations of said data once they are downloaded.

5. The system of claim 4 wherein said system further comprises:
    an active module table for identifying all of the active modules coupled to said data link and for storing the location of said module header tables once they are downloaded.

6. The system of claim 1 wherein said table comprises a module SYSGEN table containing a serial number and software revision number of the associated module.

7. The system of claim 1 wherein said table comprises a channel text table containing display text requirements for the channel keys of the associated module.

8. The system of claim 7 wherein said channel text table comprises a plurality of messages including a plurality of multiple character messages.

9. The system of claim 8 wherein said channel text table comprises means for connecting groups of said messages to form other messages.

10. The system of claim 9 wherein said channel text table comprises means for including variable data in said messages.

11. The system of claim 10 wherein said channel text table comprises means for adding non-text attributes to said displayed text.

12. The system of claim 1 wherein said table further comprises a channel process table for each channel, said channel process table including a plurality of control programs for executing preselected functions associated with said control keys and said data received from said module.

13. The system of claim 1 wherein said table comprises a channel parse table which defines the parameters of the control keys of the associated channel.

14. The system of claim 1 wherein said channel parse table further comprises information to relate preselected control keys to particular control programs in said channel process program and to particular text information in said channel text table.

15. The system of claim 1 wherein said table comprises a channel status table which includes the specific operation parameters of an associated channel at any point in time.

16. The system of claim 14 wherein said table comprises a channel control table which includes the specific operating parameters of an associated channel at any point in time, said channel control table responsive to said channel process table and said module for changing the operating parameters of the channel in response to activation of preselected ones of said control keys.

17. The system of claim 1 wherein said system further comprises a channel waveform buffer for storing a preselected interval of waveform data associated with a channel of said module.

18. The waveform buffer of claim 17 wherein said preselected interval is greater than six seconds.

19. A method for monitoring signals with at least one parameter measuring module and for displaying data associated with each channel of said module at an information processing and display station to which said module is coupled over a data link, said information processing and display station having a plurality of control keys and ;a display device, said method comprising the step of:
    downloading program instructions and channel information from said module to said station during module initialization on said data link to control the operation of said station and to define the number, functionality and visual attributes of said control keys and data associated with each channel of said module to be displayed, whereby the data of each channel are displayed by said display station independently of the functions of the other channels.

20. The method of claim 19 wherein the step of downloading comprises the step of downloading a module text table which defines all the text to be displayed for the control keys of the channels of said module.

21. The method of claim 20 wherein the step of downloading comprises the step of downloading a channel parse table for each channel of said module which defines all the parameters of each key associated with the channel.

22. The method of claim 21 wherein the step of downloading comprises the steps of downloading a channel process table comprising a plurality of controls programs which are activated in response to said control keys.

23. The method of claim 22 wherein said step of downloading comprises the step of downloading a channel control table which modifies the operating parameters of said channel in response to activation of preselected ones of said control keys.

24. A signal monitoring system, comprising:
a plurality of patient parameter measuring modules located in the vicinity of a patient, each of said modules measuring a respective physiological parameter of the patient and generating patient parameter data corresponding thereto, each of said modules further including a program memory storing a set of program instructions and a set of module data to define the characteristics of said module, said program instructions, module data and patient parameter data for each module being output on a respective data port;
a data link connected to the data ports of said patient parameter measuring module; and
a central processing and display station located away from the vicinity of the patient and connected to said modules through said data link, said station having a read/write memory into which said program instructions and module data are written, and a processing unit for causing said station to process and display said patient parameter data according to said program instructions and module data stored in said read/write memory.

25. The signal monitoring system of claim 24 wherein the data port of each module is a serial data port, and wherein said data link is a serial data link connected to all of said modules and to said central processing and display station.

26. A method of monitoring a signal, comprising:
providing at least one patient parameter measuring modules located in the vicinity of a patient, said module measuring a physiological parameter of the patient and generating patient parameter data corresponding thereto, said module further including a program memory storing a set of program instructions and a set of module data to define the characteristics of said module;
providing a central processing and display station located away from the vicinity of the patient, said station having a read/write memory and a processing unit for causing said station to process and display data according to program instructions and data stored in said read/write memory;
transferring said patient parameter data from said module to said central processing and display station; and
downloading said program instructions and module data from the program memory of said module to the read/write memory of said central processing and display station so that said station displays said patient parameter data according to said program instructions and module data downloaded to said read/write memory.

27. The method of claim 26 wherein a plurality of said patient parameter mesuring modules are connected to said central processing and display station.

28. The method of claim 27 wherein said program instructions and module data are downloaded over a single data line connecting said central processing and display station and all of said patient parameter measuring modules.

* * * * *

UNITED STATES PATENT AND TRADEMARK OFFICE
CERTIFICATE OF CORRECTION

PATENT NO. : 4,804,950

DATED : February 14, 1989

INVENTOR(S) : James B. Moon; Don L. Clark

It is certified that error appears in the above-identified patent and that said Letters Patent is hereby corrected as shown below:

In claim 19, column 24, line 56, delete ";a", substitute therefor --a--.

In claim 27, column 26, line 34, delete "mesuring", substitute therefor --measuring--.

Signed and Sealed this

Seventh Day of May, 1991

Attest:

HARRY F. MANBECK, JR.

Attesting Officer

Commissioner of Patents and Trademarks